United States Patent [19]
Matzke et al.

[11] Patent Number: 6,133,260
[45] Date of Patent: Oct. 17, 2000

[54] **USE OF 7-(2-OXA-5,8-DIAZABICYCLO[4.3.0] NON-8-YL)-QUINOLONE CARBOXYLIC ACID AND NAPHTHYRIDON CARBOXYLIC ACID DERIVATIVES FOR THE TREATMENT OF *HELICOBACTER PYLORI* INFECTIONS AND ASSOCIATED GASTRODUODENAL DISEASES**

[75] Inventors: Michael Matzke, Wuppertal; Uwe Petersen, Leverkusen; Thomas Jaetsch, Köln; Stephan Bartel, Kürten; Thomas Schenke, Bergisch Gladbach; Thomas Himmler, Odenthal-Glöbusch; Bernd Baasner, Bergisch Gladbach; Hans-Otto Werling, Wuppertal; Klaus Schaller, Wuppertal; Harald Labischinski, Wuppertal, all of Germany

[73] Assignee: Bayer Aktiengesellschaft, Leverkusen, Germany

[21] Appl. No.: 09/319,888

[22] PCT Filed: Dec. 4, 1997

[86] PCT No.: PCT/EP97/06781

§ 371 Date: Jun. 14, 1999

§ 102(e) Date: Jun. 14, 1999

[87] PCT Pub. No.: WO98/26779

PCT Pub. Date: Jun. 25, 1998

[30] Foreign Application Priority Data

Dec. 16, 1996 [DE] Germany ............ 196 52 239

[51] Int. Cl.$^7$ .................. C07D 265/28; A61K 31/5365
[52] U.S. Cl. ........................ 514/230.5; 544/105
[58] Field of Search .............. 544/105; 514/230.5

[56] References Cited

U.S. PATENT DOCUMENTS

| | | | |
|---|---|---|---|
| 4,822,801 | 4/1989 | Domagala et al. | 514/312 |
| 4,889,857 | 12/1989 | Araki et al. | 514/235.2 |
| 4,908,366 | 3/1990 | Schriewer et al. | 514/252 |
| 4,988,709 | 1/1991 | Ogata et al. | 514/314 |
| 4,990,517 | 2/1991 | Petersen et al. | 514/300 |
| 5,037,834 | 8/1991 | Brighty et al. | 514/292 |
| 5,059,597 | 10/1991 | Petersen et al. | 514/224.5 |
| 5,091,384 | 2/1992 | Kim et al. | 514/215 |
| 5,140,033 | 8/1992 | Schriewer et al. | 514/312 |
| 5,147,873 | 9/1992 | Kleinman | 514/230.2 |
| 5,164,402 | 11/1992 | Brighty | 514/300 |
| 5,229,396 | 7/1993 | Brighty | 514/300 |
| 5,252,734 | 10/1993 | Schriewer et al. | 544/64 |
| 5,385,906 | 1/1995 | Gammill et al. | 514/258 |
| 5,407,932 | 4/1995 | Kuramoto et al. | 514/210 |
| 5,416,096 | 5/1995 | Petersen et al. | 514/312 |
| 5,498,615 | 3/1996 | Kim et al. | 514/300 |
| 5,508,278 | 4/1996 | Jaetsch et al. | 514/229.2 |
| 5,532,239 | 7/1996 | Pruna | 514/254 |
| 5,563,138 | 10/1996 | Ueda et al. | 514/254 |
| 5,591,744 | 1/1997 | Ueda et al. | 514/252 |
| 5,607,942 | 3/1997 | Petersen et al. | 546/200 |
| 5,654,318 | 8/1997 | Takemura et al. | 514/314 |
| 5,672,600 | 9/1997 | Demuth, Jr. et al. | 514/224.5 |

FOREIGN PATENT DOCUMENTS

| | | |
|---|---|---|
| 235762 | 3/1986 | European Pat. Off. . |
| 276700 | 1/1988 | European Pat. Off. . |
| 0 276 700 | 8/1988 | European Pat. Off. . |
| 350733 | 1/1990 | European Pat. Off. . |
| 391132 | 10/1990 | European Pat. Off. . |
| 550903 | 7/1993 | European Pat. Off. . |
| 603887 | 6/1994 | European Pat. Off. . |
| 676199 | 10/1995 | European Pat. Off. . |
| 43 29 600 | 3/1995 | Germany . |
| 2289674 | 11/1995 | United Kingdom . |

OTHER PUBLICATIONS

NIH Consensus Statement, vol. 12, No. 1, Feb. 1994.
D.J. Hardy, et al., Journal of Antimicrobial Chemotherapy (1988), 22, 631–636.
A.E. Simor, et al., Antimicrobial Agents and Chemotherapy, Jan. 1989, pp. 108–109.
Translation of JP 188080/91.
C.St. Goodwin et al., Int. Journal of Syst. Bacteriology, 1989, pp. 397–405.
C.St. Goodwin/B.W. Worsley, The Helicobacter Genus, 1993.
A. Lee, et al., Gastroenterology, 1990, vol. 99, No. 5, pp. 1315–1323.
Abstract of JP 08 04 8629–A.

*Primary Examiner*—Mukund J. Shah
*Attorney, Agent, or Firm*—Norris, McLaughlin & Marcus, P.A.

[57] ABSTRACT

The invention relates to the use of quinolone- and naphthyridonecarboxylic acid derivatives which are substituted in the 7-position by a 2-oxa-5,8-diazabicyclo[4.3.0]-non-8-yl) radical, and their pharmaceutically utilizable hydrates and/or salts for the therapy of Helicobacter pylori infections and the gastroduodenal disorders associated therewith.

3 Claims, No Drawings

USE OF 7-(2-OXA-5,8-DIAZABICYCLO[4.3.0] NON-8-YL)-QUINOLONE CARBOXYLIC ACID AND NAPHTHYRIDON CARBOXYLIC ACID DERIVATIVES FOR THE TREATMENT OF *HELICOBACTER PYLORI* INFECTIONS AND ASSOCIATED GASTRODUODENAL DISEASES

The invention relates to the use of quinolone- and naphthyridonecarboxylic acid derivatives which are substituted in the 7-position by a 2-oxa-5,8-diazabicyclo[4.3.0] non-8-yl radical, and their salts for the therapy of Helicobacter pylori infections and the gastroduodenal disorders associated therewith.

With the rediscovery of *Helicobacter pylori* (*H. pylori*; formally Campylobacter pylori) by Warren and Marshall in 1983, in the following years it was possible to fundamentally further develop the pathophysiological ideas about the origin of gastroduodenal disorders of man.

*H. pylori* is regarded as a cause of type B gastritis and appears to play a causal role in the perpetuation of peptic ulcer. Epidemiological and pathological investigations likewise point to a relationship between long-term colonization of the gastric mucosa with the bacterium and the origin of certain forms of carcinoma of the stomach. *H. pylori* was therefore classified in 1994 as a carcinogen of the first class (most dangerous carcinogenic category). A rare stomach cancer, MALT lymphoma (mucosa-associated lymphoid tissue), likewise often appears to be caused by the bacterium. In initial case reports, after *H. pylori* eradication not only the reactive infiltrates actually disappeared, but also a part of the poorly malignant MALT lymphoma. Relationships with hypertrophic gastritis are also discussed. The role of *H. pylori* in functional gastropathy (nonulcerative dyspepsia) is still unclear.

Various epidemiological studies come to the conclusion that about half the world population is infected with the bacterium. The probability of the colonization of the stomach with Helicobacter increases with age. The optimum adaptation of Helicobacter to the living conditions in the unusual, low-competition habitat [lacuna] stomach appears to be the prerequisite for the successful establishment of the chronic infection and for the wide distribution of this pathogenic species.

The pathogenic organisms with their flagella are very mobile not only in the liquid medium, but also in the viscous mucus of the gastric mucous membrane, adhere to the gastric epithelial cells and proliferate best at an oxygen content of 5%, as prevails in the mucus of the gastric wall. Moreover, the bacteria form large amounts of the enzyme urease, which splits urea into ammonia and carbon dioxide. Possibly, the resulting 'ammonia cloud' helps to neutralize the acidic medium in the microenvironment and thus to protect from the aggressive gastric acid.

Peptic Ulcer

The introduction of the histamine $H_2$ receptor antagonists in the 70s was a milestone in the therapy of peptic ulcer. The frequency of surgical interventions for treatment of the ulcer sufferer thus decreased dramatically worldwide. This principle of acid blockage was improved still further by the development of the even more strongly active proton pump inhibitors As a result of the antacid therapy, however, only the symptoms of the ulcer, not the natural course of the disorder, which is characterized by the occurrence of relapses, can be influenced causally—say due to bactericidal treatment. Since virtually all duodenal ulcer patients and the predominant majority of patients with stomach ulcer have an *H. pylori* infection of the stomach and thus suffer from infectious diseases. Only ulcerations which are caused by non-steroidal anti-inflammatories are not associated with an *H. pylori* infection.

Therefore, according to the recommendations of a consensus conference, which was organized in 1994 by the American Public Health Authority (NIH), in the case of positive detection of bacteria all patients with peptic ulcers should be subjected to eradication therapy directed against *H. pylori* (NIH Consensus Statement 1: 1–23; 1994). The arguments were supplied by controlled therapy studies, in which it was possible to show that after successful eradication of bacteria the ulcer recurrence rates fall drastically (0%–29% versus 61%–95%).

*H. pylori* Therapy

The present eradication of *H. pylori* turns out to be problematic in practice. A simple and yet reliably effective therapy is not available. The bacterium turns out to be well protected and difficult to attack under the mucous layer.

*H. pylori* is sensitive in vitro to numerous antibiotics. These are, however, not effective in vivo as a monotherapy. These include, inter alia, penicillin, amoxicillin, tetracyclin, erythromycin, ciprofloxacin, metronidazole and clarithromycin. Bismuth salts and, to a small extent, even proton pump inhibitors (omeprazole, lansoprazole) are antibacterially active in vitro, but not in vivo.

Among all therapy modalities hitherto used for the eradication of *H. pylori*, at present only the following triple therapies are sufficiently active:

1. classical bismuth triple therapy (bismuth salt plus two antibiotics) and the
2. modified triple therapy (acid inhibitor plus two antibiotics).

However, these regimes are involved eradication procedures with poor compliance, which can be affected up to 35% by side effects (abdominal pain, nausea, diarrhoea, dryness of the mouth, taste disorders and allergic skin reactions, etc.). Wide use is therefore made difficult. A further great disadvantage is the high number of medicaments to be taken daily (12–16 tablets/day). This is particularly marked in the quadruple therapy, in which an acid secretion inhibitor is administered simultaneously to the classical triple therapy.

The better tolerated dual therapy propagated in Germany (combination of amoxicillin with omeprazole) is, however, only poorly effective and appears to fail even largely in patients pretreated with omeprazole and in smokers.

In the triple therapies, the antibiotic components as a rule administered are amoxicillin, nitroimidazole compounds (metronidazole, tinidazole), tetracyclin and recently macrolides (clarithromycin) [in 3–4 sub-doses].

Worldwide, eradication rates of 70–90% are achieved. Various factors can, however, influence this eradication result:

1. In the first place, the resistance of the bacterium (developing countries: up to 60%, Germany: up to 10%) against metronidazole, the most frequently employed antibiotic in triple therapy, can be mentioned. Even in the case of treatment with clarithromycin, the disadvantage of a development of resistance of up to 10% is to be pointed out.
2. As a further factor, the abovementioned compliance of the patients can be mentioned.

Animal Model

An *H. felis* mouse model has been described as a suitable animal model [A. Lee et al., Gastroentrology 99: 1315–1323

(1990)] and has been modified by us so that it is very highly suitable for the screening and the comparative assessment of abovementioned compounds.

In spite of large morphological differences, the corkscrew-like, urease-forming bacterium *H. felis* is very closely related to *H. pylori*. *H. felis* is a natural inhabitant of the gastric mucosa of dogs and cats. After oral inoculation, the pathogenic bacteria also colonize the mouse stomach in a similar manner to that in which *H. pylori* colonizes the stomach of man. The established chronic long-term infection leads in mice to active gastritis and induces a corresponding immune response.

The therapeutic effectiveness of test preparations determined in the *H. felis* mouse model is regarded in the literature as predictive of the corresponding clinical efficacy.

In spite of very good in-vitro activity of antibiotics (e.g. amoxicillin or erythromycin) against *H. pylori*, after monotherapeutic use clinically these show no significant therapeutic action. This fact is also repeated by the *H. felis* mouse model. Correspondingly, it was also possible to confirm the clinically recognized eradicative action of the classical triple therapy in the *H. felis* mouse model.

Antibacterially active 7-(2-oxa-5,8-diazabicyclo[4.3.0] non-8-yl)-quinolone- and naphthyridonecarboxylic acid derivatives have already been disclosed in EP-A-350733 and EP-A-550 903 (Bayer). In JP 8048629 (Dainippon), it was described that compounds such as 8-chloro-1-cyclopropyl-7-([S,S]-2,8-diazabicyclo[4.3.0]non-8-yl)-6-fluoro-1,4-dihydro-4-oxo-3-quinolinecarboxylic acid (BAY Y 3118) have an antibacterial action against *H. pylori*. It is also known that a number of highly active quinolones, such as, for example, ciprofloxacin, lomefloxacin or ofloxacin (Journal of Antimicrobial Chemotherapy 22, 631–636 [1988], Antimicrobial Agents and Chemotherapy, 33, 108–109 [1989]), have an action against Helicobacter spp. in vitro. It was seen, however, in the animal model (Helicobacter felis, mouse), that these clinically employed antibacterially active quinolones in therapeutically used doses are not able to lead to an eradication of the bacterium. Even by a monotherapeutic treatment with highly active quinolones, which hitherto have not been introduced into the market, such as, for example, with the already mentioned BAY Y 3118, no eradication of *H. felis* can be achieved in the mouse model without in the main a large part of the animals not dying on account of the toxicity of the compound. The use of trovafloxacin or its derivatives in combination with other antibiotics such as amoxicillin or tetracyclines or proton pump inhibitors such as omeprazole for the therapy of *H. pylori* is described in EP-676 199 and GB-A-2 289 674 (Pfizer).

The object on which the invention is based was therefore to find relatively highly tolerable active compounds which are able to eradicate this highly specialized bacterium by a simple monotherapy.

It has now been found that compounds of the general formula (I)

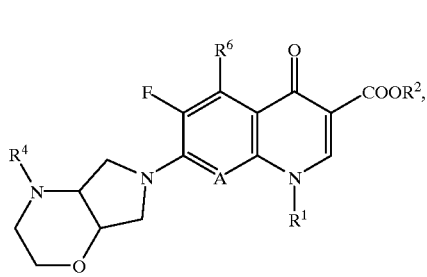

in which
R$^1$ represents alkyl having 1 to 4 C atoms, which is optionally mono- or disubstituted by halogen, phenyl which is optionally substituted by 1 or 2 fluorine atoms or cyclopropyl which is optionally substituted by 1 or 2 fluorine atoms, R$^2$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl, A represents N or C—R$^3$, where R$^3$ represents hydrogen, halogen, methyl, methoxy, difluoromethoxy or cyano alternatively, together with R$^1$, can form a bridge of the structure —*O—CH$_2$—CH—CH$_3$ or —*O—CH$_2$—N—CH$_3$, where the atom marked by * is connected to the carbon atom of A, R$^4$ represents hydrogen, benzyl. C$_1$-C$_3$-alkyl, (5-methyl-2-oxo-1,3-dioxol-4-yl)-methyl, radicals of the structures —CH=CH—COOR$^5$, —CH$_2$CH$_2$COOR$^5$, —CH$_2$CH$_2$CN, —CH$_2$CH$_2$COCH$_3$, —CH$_2$COCH$_3$, in which R$^5$ represents methyl or ethyl, R$^6$ represents hydrogen, amino, hydroxyl, methyl or halogen, in the form of racemates, diastereomer mixtures or as enantiomerically pure or diastereomerically pure compounds, their pharmaceutically utilizable hydrates and/or salts, such as acid addition salts and the alkali metal, alkaline earth metal, silver and guanidinium salts of the carboxylic acids on which they are based, have a high antibacterial action against Helicobacter spp. and can be used for the eradication of this pathogenic bacterium.

Preferred compounds of the formula (I) are those in which

R$^1$ represents tert-butyl which is optionally mono- or disubstituted by fluorine or cyclopropyl which is optionally substituted by 1 fluorine atom, R$^2$ represents hydrogen, alkyl having 1 to 4 carbon atoms or (5-methyl-2-oxo-1,3-dioxol-4-yl)-methyl, A represents C—R$^3$, where R$^3$ represents hydrogen, fluorine, methoxy, difluoromethoxy, cyano alternatively, together with R$^1$, can form a bridge of the structure —*O—CH$_2$—CH—CH$_3$ or —*O—CH$_2$—N—CH$_3$, where the atom marked by * is connected to the carbon atom of A, R$^4$ represents hydrogen, C$_1$-C$_3$-alkyl, radicals of the structures, —CH$_2$CH$_2$COOR$^5$, —CH$_2$CH$_2$CN, —CH$_2$COCH$_3$, in which R$^5$ represents methyl or ethyl, R$^6$ represents hydrogen, amino or methyl, and their pharmaceutically utilizable hydrates and/or salts such as acid addition salts and the alkali metal alkaline earth metal silver and guanidinium salts of the carboxylic acids on which they are based.

Particularly preferred compounds of the formula (I) are those in which $R^1$ represents tert-butyl which is optionally mono- or disubstituted by fluorine, or cyclopropyl, $R^2$ represents hydrogen, methyl or ethyl, A represents C—$R^3$, where $R^3$ represents hydrogen, methoxy, difluoromethoxy, cyano alternatively, together with $R^1$, can form a bridge of the structure —*O—CH$_2$—CH—CH$_3$ or —*O—CH$_2$—N—CH$_3$, where the atom marked by * is connected to the carbon atom of A, $R^4$ represents hydrogen or methyl, $R^6$ represents hydrogen, and their pharmaceutically utilizable hydrates and/or salts, such as acid addition salts, and the alkali metal, alkaline earth metal, silver and guanidinium salts of the carboxylic acids on which they are based.

The present invention also relates to the new compounds 8-cyano-1-cyclopropyl-6-fluoro-7-(2-oxa-5,8-diazabicyclo [4.3.0]non-8-yl)-1,4-dihydro-4-oxo-3-quinolinecarboxylic acid and 1-cyclopropyl-8-difluoromethoxy-6-fluoro-1,4-dihydro-7-(2-oxa-5,8-diazabicyclo[4.3.0]non-8-yl)-4-oxo-3-quinolinecarboxylic acid, in particular in diastereomerically pure and enantiomerically pure form, and their pharmaceutically utilizable hydrates and/or salts, such as acid addition salts, and the alkali metal, alkaline earth metal, silver and guanidinium salts of the carboxylic acids on which they are based. 8-Cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic acid is particularly preferred.

The compounds which are suitable for the use according to the invention are in some cases already known from EP-A-0 350 733, EP-A-0 550 903 and from DE-A-4 329 600 or can be prepared by the processes described there.

If, for example, 9,10-difluoro-3,8-dimethyl-7-oxo-2,3-dihydro-7H-pyrido-[1,2,3-d,e][1,3,4]benzoxadiazine-6-carboxylic acid and 2-oxa-5,8-diazabicyclo-[4.3.0]nonane are used, the course of the reaction can be represented by the following equation:

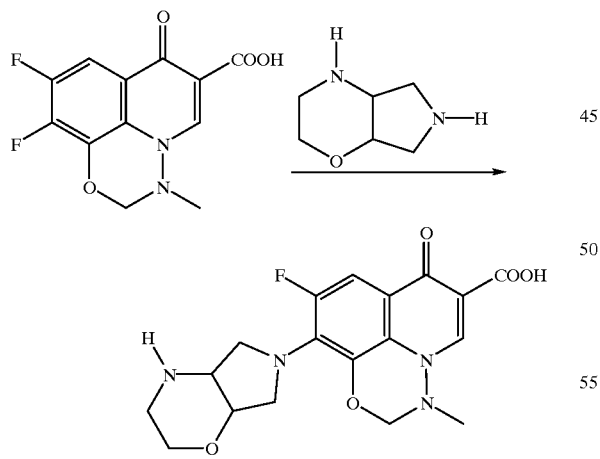

The 7-halogeno-quinolonecarboxylic acid derivatives employed for the preparation of the compounds of the formula (I) according to the invention are known or can be prepared by known methods. Thus 7-chloro-8-cyano-1-cyclopropyl-6-fluoro-1,4-dihydro-4-oxo-3-quinolinecarboxylic acid and ethyl 7-chloro-8-cyano-1-cyclopropyl-6-fluoro-1,4-dihydro-4-oxo-3-quinolinecarboxylate have been described in EP-A-0 276 700. The corresponding 7-fluoro derivatives can also be synthesized, for example, via the following reaction sequence:

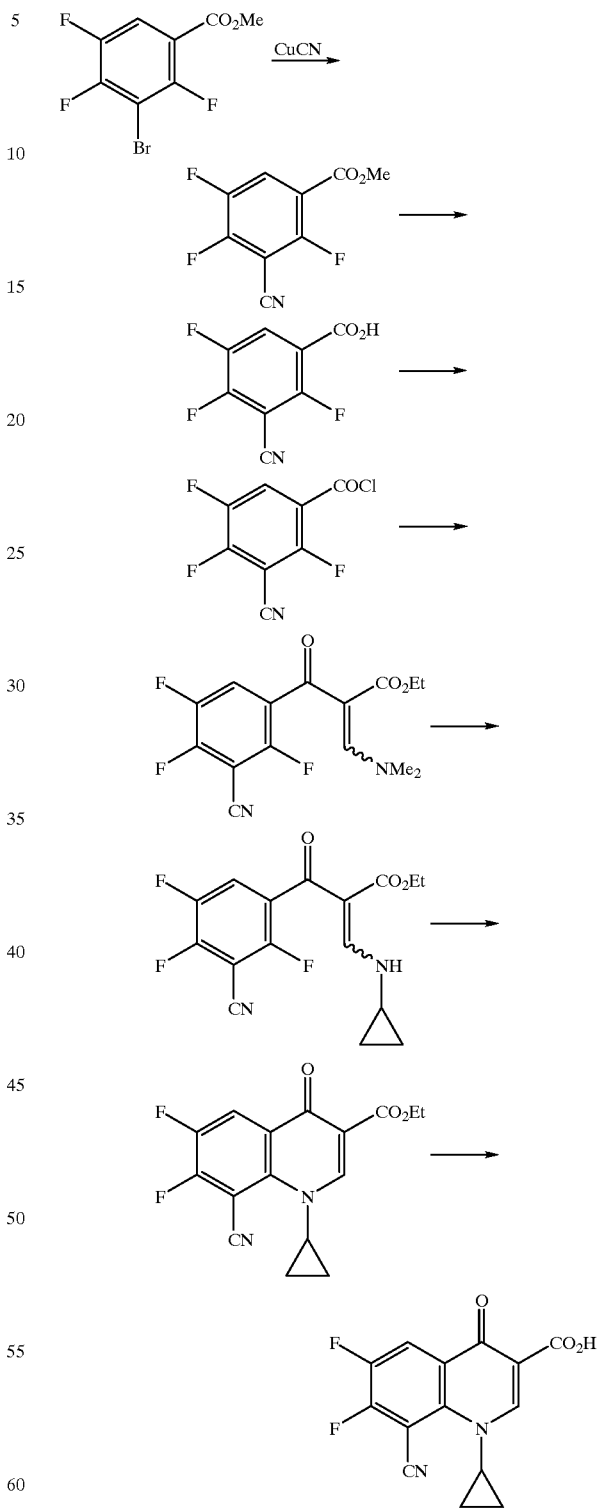

An alternative process for the preparation of the intermediate compound 2,4-dichloro-3-cyano-5-fluoro-benzoyl chloride, which serves as a starting material for the preparation of 7-chloro-8-cyano-1-cyclopropyl-6-fluoro-1,4-dihydro-4-oxo-3-quinolinecarboxylic acid (EP-A-0 276

700) and which can converted into 3-cyano-2,4,5-trifluoro-benzoyl fluoride, starts from 5-fluoro-1,3-xylene: 5-fluoro-1,3-xylene is dichlorinated in the nucleus under ionic conditions in the presence of a catalyst to give 2,4-dichloro-5-fluoro-1,3-dimethylbenzene and this is then chlorinated under free-radical conditions in the side chains to give 2,4-dichloro-5-fluoro-3-dichloromethyl-1-trichloromethylbenzene. This is hydrolysed via 2,4-dichloro-5-fluoro-3-dichloromethylbenzoic acid to give 2,4-dichloro-5-fluoro-3-formyl-benzoic acid and then reacted to give 2,4-dichloro-5-fluoro-3-N-hydroxyiminomethyl-benzoic acid. By treatment with thionyl chloride, 2,4-dichloro-3-cyano-5-fluoro-benzoyl chloride is obtained, which can additionally be reacted by means of a chlorine/fluorine exchange to give 3-cyano-2,4,5-trifluoro-benzoyl fluoride.

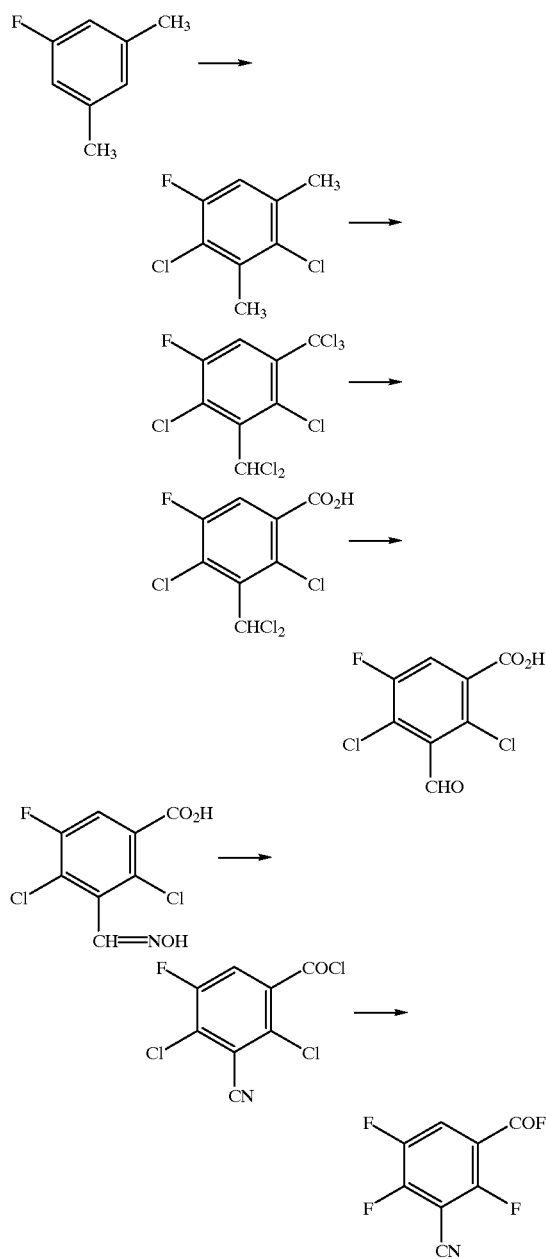

The amines employed for the preparation of the compounds of the formula (I) according to the invention are known from EP-A-0 550 903, EP-A-0 551 653 and from DE-A-4 309 964.

An alternative to the synthesis of 1S,6S-2-oxa-5,8-diazabicyclo[4.3.0]nonane dihydrobromide or of the free base 1S,6S-2-oxa-5,8-diazabicyclo[4.3.0]nonane and the corresponding 1R,6R enantiomer is the following route:

The starting material for this synthesis is cis-1,4-dihydroxy-2-butene, which is reacted to give 1-tosylpyrrolidine after mesylation to the bis-mesylate with tosylamide. This is converted into the epoxide [lacuna] m-chloroperbenzoic acid. The ring-opening of the epoxide is carried out by heating with ethanolamine in isopropanol to give trans-3-hydroxy-4-(2-hydroxy-ethylamino)-1-(toluene-4-sulphonyl)-pyrrolidinein over 80% yield. The latter is then reacted with tosyl chloride in pyridine/tetrahydrofuran with cooling to give the tris-tosylate, which is cyclized under basic reaction conditions as a crude product mixed with some tetra-tosyl derivative to give racemic trans-5,8-bis-tosyl-2-oxa-5,6-diazabicyclo[4.3.0]nonane. At this stage, a chromatographic resolution is carried out with high selectivity on silica gel-bonded poly(N-methacryloyl-L-leucine-d-menthylamide) as the stationary phase. The desired enantiomer, (1S,6S)-5,8-bis-tosyl-2-oxa-5,6-diazabicyclo[4.3.0]nonane, is isolated with a purity of >99% ee. The removal of the p-tosyl protective groups is carried out using HBr-glacial acetic acid to give 1S,6S-2-oxa-5,8-diazabicyclo[4.3.0]nonanedihydrobromide, which can be converted into the free base using bases such as, for example, sodium or potassium hydroxide or with the aid of an ion exchanger. The analogous reaction sequence can also be used for the preparation of 1R,6R-2-oxa-5,8-diazabicyclo[4.3.0]nonane dihydrobromide.

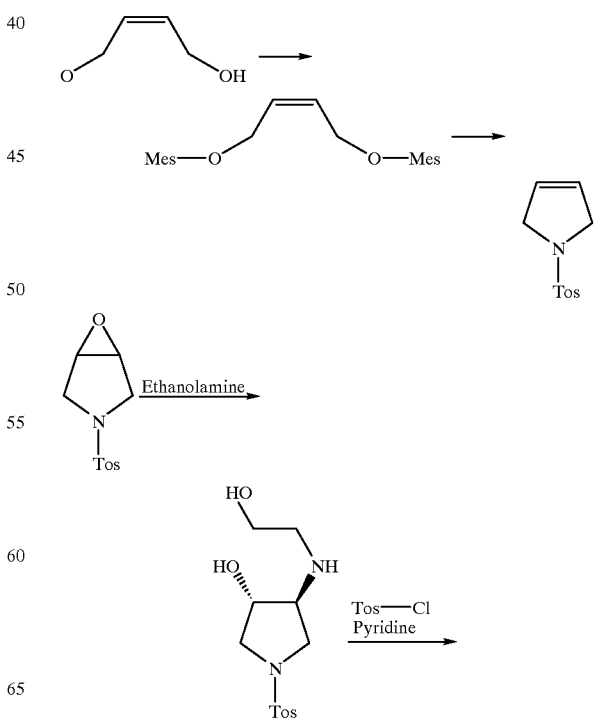

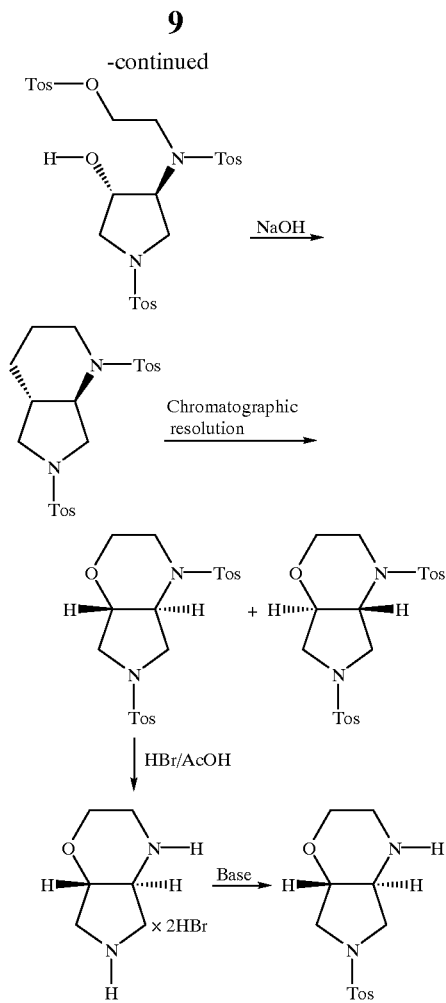

Synthesis of 1S,6S-2-oxa-5,8-diazabicyclo[4.3.0]Nonane

Examples of compounds according to the invention which may be mentioned apart from the compounds mentioned in the preparation examples are the compounds mentioned in Table 1 below, which can be used both in racemic form and as enantiomerically pure or diastereomerically pure compounds.

TABLE 1

| A | $R^4$ | $R^6$ |
|---|---|---|
| C—H | H | $CH_3$ |
| C—H | $CH_3$ | H |
| C—CN | H | $CH_3$ |
| C—CN | H | $NH_2$ |
| C—CN | H | OH |
| C—CN | H | F |
| C—CN | $CH_3$ | H |
| C—CN | $CH_3$ | $CH_3$ |
| C—CN | $CH_3$ | $NH_2$ |
| C—CN | $CH_3$ | OH |
| C—CN | $CH_3$ | F |
| C—$OCH_3$ | H | $CH_3$ |
| C—$OCH_3$ | H | $NH_2$ |
| C—$CH_3$ | H | $NH_2$ |
| C—$CH_3$ | H | $CH_3$ |

The compounds according to the invention can crystallize in the form of their betaines or in the form of the salts having one to two mol of water.

The compounds according to the invention have a strongly antibiotic action and exhibit, together with low toxicity, a broad antibacterial spectrum against gram-positive and gram-negative microorganisms, above all, however, also against Helicobacter spp.

These valuable properties make possible their use as chemotherapeutic active compounds for the therapy of Helicobacter pylori infections and the gastroduodenal disorders associated therewith, which can be prevented, ameliorated and/or cured by the compounds according to the invention.

The compounds according to the invention can be used in various pharmaceutical preparations. Preferred pharmaceutical preparations which may be mentioned are tablets, coated tablets, capsules, pills, granules, solutions, suspensions and emulsions.

Although the compounds according to the invention are employed as monotherapeutic agents, if required they can also be used in combination with other therapeutics. By way of example, the following may be mentioned as combination components: nitroimidazole derivatives, for example metronidazole; proton pump inhibitors, for example omeprazole, pantoprazole or lansoprazole; $H_2$ receptor antagonists, such as, for example, cimetidine, ranitidine, famotidine or nizatidine; bismuth compounds, such as, for example, bismuth salicylate or CBS (colloidal bismuth subcitrate); other antibiotics, such as, for example, amoxicillin, azlocillin or clarithromycin; antacids.

The minimal inhibitory concentrations (MIC), which are listed in Table 2 by way of example in comparison to ciprofloxacin for some of the compounds according to the invention, were determined in the agar dilution test on Columbia agar or Basis 2 agar (Oxoid) with 10% lysed horse blood either at pH 7 or pH 5 with 1 g/l of urea. The test substances were tested in replica dishes, which contained falling concentrations of the active compound at in each case doubled dilution. For inoculation, fresh Helicobacter cultures from liquid culture or suspension of the bacteria from agar plates were used. The inoculated agar plates were incubated at 37° C. in an atmosphere containing 5–10% of $CO_2$ for 48–72 hours. The MIC value (mg/l) which was read off indicates the lowest active compound concentration at which no growth was to be detected using the naked eye. The following Helicobacter isolates were used: *H. felis*

ATCC 49179, *H. pylori* NCTC 11637, *H. pylori* clinical isolate 008.

TABLE 2

MIC values (mg/l) of some compounds according to the invention (agar dilution test)

| Example | MIC (mg/l) | |
|---|---|---|
| | *H. pylori* 008 | *H. pylori* 11637 |
| 1A | 0.06 | n.d. |
| 2 | 0.06 | n.d. |
| 4 | 0.25 | 0.06 |
| 6 | 0.06 | 0.06 |
| 8 | 0.06 | 0.06 |
| 13 | 0.125 | 0.06 |
| Ciprofloxacin | 0.125 | 0.125 |

For investigations in the animal model, female Swiss mice (8 to 12 weeks old, SPF breeding) were kept using commercially available feed and water. A defined *H. felis* strain (ATCC 49179) was used for colonization. The bacteria are administered by stomach tube as a suspension (0.1 ml containing $10^8$–$10^9$ bacteria) 4 times in the course of 7 days. Alternatively to this, stomach homogenates of previously infected mice were used for infection.

3–5 days after establishment of the infection, the treatment with test preparations was begun. As a first treatment result, the bacterial reduction was determined as "clearance" 24 hours after the last treatment (for example 3, 7, 10, 14 days; 1–3 times daily). In some cases, the bacterial eradication was also determined 2–4 weeks after the end of treatment. Following the "CLO" test used in clinical diagnosis, a urease test on a microtitre basis was employed. Defined stomach biopsy samples were tested for colour change within 24 hours.

In Table 3, as an example of the surprisingly high in-vivo action of the compounds according to the invention, the therapeutic result after 7 days' treatment of infected mice with 8-cyano-1-cyclopropyl-6-fluoro-7-((1S,6S)-2-oxa-5,8-diazabicyclo[4.3.0]-non-8-yl)-1,4-dihydro-4-oxo-3-quinolinecarboxylic acid (Example 1A) and for 9-fluoro-3-methyl-10-((1S,6S)-2-oxa-5,8-diazabicyclo[4.3.0]non-8-yl)-7-oxo-2,3-dihydro-7H-pyrido[1,2,3-d,e][1,3,4]benzoxadiazine-6-carboxylic acid (Example 2) is shown in comparison to treatment with ciprofloxacin: while with ciprofloxacin no clearance is achieved under these experimental conditions, in the compounds according to the invention this is 100%. A 10-day treatment of the mice with 2×10 mg/kg of 8-cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic acid even led to an eradication of the bacterium.

TABLE 3

Therapeutic result after 70 day treatment of infected (*H. felis* ATCC 49179) mice (5 animals per group)

| Example | Dose [mg/kg] | Clearance | % |
|---|---|---|---|
| 1 | 2 × 10 | 5/5 | 100 |
| 2 | 2 × 10 | 5/5 | 100 |
| Ciprofloxacin | 2 × 10 | 0/5 | 0 |

EXAMPLES

Preparation of the Intermediates

Example Z 1

Ethyl 8-cyano-1-cyclopropyl-6,7-difluoro-1,4-dihydro-4-oxo-3-quinoline-carboxylate

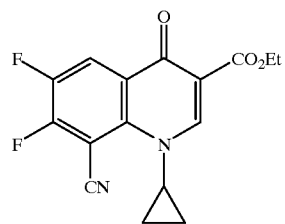

a. Methyl 3-bromo-2,4,5-trifluoro-benzoate:

772 g of 3-bromo-2,4,5-trifluoro-benzoylfluoride are added dropwise with ice-cooling to a mixture of 1460 ml of methanol and 340 g of triethylamine. Stirring is carried out at room temperature for 1 hour. The reaction mixture is concentrated, the residue is taken up in water and methylene chloride, and the aqueous phase is again extracted by shaking with methylene chloride. After drying the organic phase over sodium sulphate, it is concentrated and the residue is distilled in vacuo. 752.4 g of methyl 3-bromo-2,4,5-trifluoro-benzoate of boiling point 122° C./20 mbar are obtained.

b. Methyl 3-cyano-2,4,5-trifluoro-benzoate:

269 g of methyl 3-bromo-2,4,5-trifluoro-benzoate and 108 g of copper cyanide are heated to reflux for 5 hours in 400 ml of dimethylformamide. All volatile constituents of the reaction mixture are then removed by distillation in vacuo. The distillate is then fractionated on a column. 133 g of methyl 3-cyano-2,4,5-trifluoro-benzoate of boiling point 88–89° C./0.01 mbar are obtained.

c. 3-Cyano-2,4,5-trifluoro-benzoic acid:

A solution of 156 g of methyl 3-cyano-2,4,5-trifluoro-benzoate in 960 ml of glacial acetic acid, 140 ml of water and 69 ml of concentrated sulphuric acid is heated to reflux for 8 hours. The acetic acid is then largely removed by distillation in vacuo and the residue is treated with water. The precipitated solid is filtered off with suction, washed with water and dried. 118.6 g of 3-cyano-2,4,5-trifluoro-benzoic acid are obtained as a white solid of melting point 187–190° C.

d. 3-Cyano-2,4,5-trifluoro-benzoyl chloride:

111 g of 3-cyano-2,4,5-trifluoro-benzoic acid and 84 g of oxalyl chloride are stirred at room temperature for 5 hours in 930 ml of dry methylene chloride with addition of a few drops of dimethylformamide. The methylene chloride is then stripped off and the residue is distilled in vacuo. 117.6 g of 3-cyano-2,4,5-trifluoro-benzoyl chloride are obtained as a yellow oil.

e. Ethyl 2-(3-cyano-2,4,5-trifluoro-benzoyl)-3-dimethylamino-acrylate:

A solution of 55 g of 3-cyano-2,4,5-trifluoro-benzoyl chloride in 50 ml of toluene is added dropwise to a solution of 36.5 g of ethyl 3-dimethylamino-acrylate and 26.5 g of triethylamine in 140 ml of toluene such that the temperature remains between 50 and 55° C. Stirring is then carried out at 50° C. for a further 2 hours. The reaction mixture is concentrated in vacuo and employed in the next stage without further working up.

f. Ethyl 2-(3-cyano-2,4,5-trifluoro-benzoyl)-3-cyclopropylamino-acrylate:

30 g of glacial acetic acid are added dropwise at 20° C. to the reaction product from stage e. A solution of 15.75 g of cyclopropylamine in 30 ml of toluene is then added dropwise. The mixture is stirred at 30° C. for 1 hour. 200 ml of water are then added, the mixture is stirred for 15 minutes, and the organic phase is separated off and again extracted by shaking with 100 ml of water. The organic phase is then dried over sodium sulphate and concentrated in vacuo. The crude product thus obtained is employed in the next stage without further working up.

g. Ethyl 8-cyano-1-cyclopropyl-6,7-difluoro-1,4-dihydro-4-oxo-3-quinoline-carboxylate:

The reaction product from stage f and 27.6 g of potassium carbonate are stirred at room temperature for 16 hours in 80 ml of dimethylformamide. The reaction mixture is then added to 750 ml of ice water, and the solid is filtered off with suction and washed with 80 ml of cold methanol. After drying, 47 g of ethyl 8-cyano-1-cyclopropyl-6,7-difluoro-1,4-dihydro-4-oxo-3-quinolinecarboxylate of melting point 209–211° C. are obtained.

Example Z 2

2,4-Dichloro-5-fluoro-1,3-dimethylbenzene

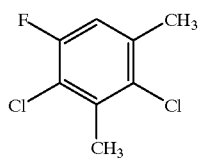

a) solvent-free 1 g of anhydrous iron(III) chloride are introduced into 124 g of 3,5-dimethyl-fluorobenzene and chlorine is passed in at the rate (about 4 h) at which the reaction proceeds. This is initially somewhat exothermic (temperature rise from 24 to 32° C.) and is kept below 30° C. by cooling. After addition of 120 g of chlorine, the mixture becomes solid. According to GC analysis, 33.4% of monochloro compound, 58.4% of desired product and 5% of overchlorinated compounds are formed. The hydrogen chloride is stripped off and the reaction mixture is then distilled on a column in a water-jet vacuum:

49 g of 2-chloro-5-fluoro-1,3-dimethylbenzene are obtained in the forerun at 72–74° C./22 mbar. After an intermediate fraction of 5 g, 75 g of 2,4-dichloro-5-fluoro-1,3-dimethylbenzene pass over at 105° C./22 mbar; melting range: 64–65° C.

b) in 1,2-dichloroethane 1 kg of 3,5-dimethyl-fluorobenzene and 15 g of anhydrous iron(III) chloride are introduced into 1 l of 1,2-dichloroethane and chlorine is passed in at the rate at which the reaction proceeds (about 4 h). The reaction is initially exothermic (temperature rise from 24 to 32° C.) and is kept below 30° C. by cooling. After passing in 1200 g of chlorine, 4% of monochloro compound, 81.1% of desired product and 13.3% of overchlorinated compounds are formed according to GC analysis. After removal of the solvent and of the hydrogen chloride by distillation, the mixture is distilled on a column in a water-jet vacuum:

40 g of 2-chloro-5-fluoro-1,3-dimethylbenzene are obtained in the forerun. After a small quantity of intermediate fraction, 1115 g of 2,4-dichloro-5-fluoro-1,3-dimethylbenzene pass over at 127–128° C./50 mbar.

Example Z 3

2,4-Dichloro-5-fluoro-3-dichloromethyl-1-trichloromethylbenzene

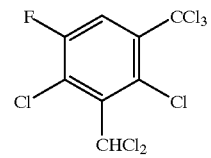

1890 g of 2,4-dichloro-5-fluoro-1,3-dimethylbenzene are introduced into a photochlorination apparatus with a chlorine inlet and outlet for the hydrogen chloride to a scrubber and a light source in the vicinity of the chlorine inlet tube and chlorine is metered in at 140 to 150° C. 3850 g of chlorine are passed in in the course of 30 h. The content of desired product according to GC analysis is 71.1%; the content of underchlorinated compounds 27.7%.

Distillation through a 60 cm column containing Wilson spirals yields a forerun of 1142 g which can be employed again in the chlorination. The main fraction at 160–168° C./0.2 mbar yields 2200 g of 2,4-dichloro-5-fluoro-3-dichloromethyl-1-trichloromethylbenzene having a melting range of 74–76° C. After recrystallization of a sample from methanol, the melting point is 81–82° C.

Example Z 4

2,4-Dichloro-5-fluoro-3-formyl-benzoic Acid

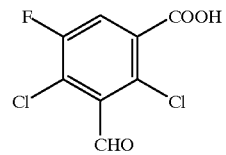

2500 ml of 95% strength sulphuric acid are introduced at 70° C. into a stirring apparatus with a gas inlet and 500 g of molten 2,4-dichloro-5-fluoro-3-dichloromethyl-1-trichloromethylbenzene are added dropwise with stirring. Evolution of hydrogen chloride commences after a short time. Metering in is carried out for 2 h and the mixture is stirred until evolution of gas has ended. After cooling to 20° C., the mixture is discharged onto 4 kg of ice and the precipitated solid is filtered off with suction. The product is washed with water and dried.

Yield: 310 g melting range: 172–174° C.

Example Z 5

2,4-Dichloro-5-fluoro-3-N-hydroxyiminomethyl-benzoic Acid

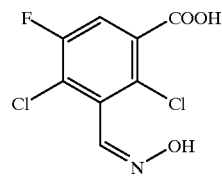

80 g of hydroxylammonium chloride in 500 ml of ethanol are introduced into a stirring apparatus and 200 ml of 45% strength sodium hydroxide solution are added dropwise and 200 g of 2,4-dichloro-5-fluoro-3-formyl-benzoic acid are then introduced at 40–45° C. The reaction is slightly exothermic and the mixture is stirred at 60° C. for 5 h. After cooling to room temperature, it is adjusted to pH <3 by dropwise addition of hydrochloric acid, the product is taken up in tert-butyl methyl ether, the organic phase is separated off and the solvent is removed by distillation. 185 g of 2,4-dichloro-5-fluoro-3-N-hydroxyiminomethyl-benzoic acid are obtained as a residue; melting range: 190–194° C.

Example Z 6
2,4-Dichloro-3-cyano-5-fluoro-benzoyl Chloride

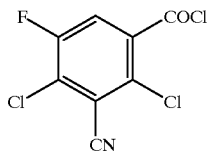

600 ml of thionyl chloride are introduced into a stirring apparatus having a metering device and gas outlet via a reflux condenser to a scrubber and 210 g of 2,4-dichloro-5-fluoro-3-N-hydroxyiminomethyl-benzoic acid are introduced at 20° C. at the rate at which hydrogen chloride and sulphur dioxide are evolved. After the addition, the mixture is heated under reflux until the evolution of gas has ended. The mixture is then distilled, and 149 g of 2,4-dichloro-3-cyano-5-fluoro-benzoyl chloride are obtained in the boiling range from 142–145° C./10 mbar (purity according to GC 98.1%); melting range: 73–75° C.

Example Z 7
3-Cyano-2,4,5-trifluoro-benzoyl Fluoride

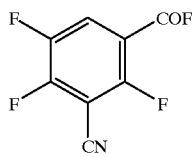

50 g of potassium fluoride are suspended in 120 ml of tetramethylene sulphone and the mixture is subjected to incipient distillation to dryness at 15 mbar (about 20 ml). 50.4 g of 2,4-dichloro-3-cyano-5-fluoro-benzoyl chloride are then added and the mixture is stirred at an internal temperature of 180° C. for 12 hours with exclusion of moisture. 32.9 g of 3-cyano-2,4,5-trifluoro-benzoyl fluoride are obtained in the boiling range from 98–100° C./12 mbar by vacuum distillation.

Example Z 8
3-Cyano-2,4,5-trifluoro-benzoyl Chloride

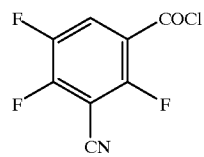

76.6 g of 3-cyano-2,4,5-trifluoro-benzoyl fluoride are introduced at 60–65° C. together with 1 g of anhydrous aluminum chloride and then 25 g of silicon tetrachloride are added dropwise in the course of the evolution of gas. After the evolution of gas at 65° C. has ended, the mixture is distilled in vacuo. 73.2 g of 3-cyano-2,4,5-trifluoro-benzoyl chloride pass over in the boiling range from 120–122° C./14 mbar.

Example Z 9

1-(Toluene-4-sulphonyl)-pyrroline

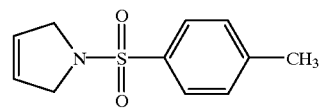

2.016 kg (17.6 mol) of methanesulphonyl chloride in 12 l of dichloromethane are introduced into a 20 l HC4 vessel with a plane-ground joint and a solution of 705 g (8.0 mol) of 2-butene-1,4-diol in 1.944 kg (2.68 l, 19.2 mol) of triethylamine is added dropwise at an internal temperature of −10° C. with vigorous cooling (−34° C.) in the course of 30 minutes. A yellow suspension is obtained which is stirred at −10° C. for 1 hour and then treated with 4 l of water, the temperature rising to 0° C. The suspension is warmed to room temperature, stirred at room temperature for 10 minutes and then collected in a 30 l separating funnel. The phases are separated (good phase separation) and the aqueous phase is washed with 2 l of dichloromethane with stirring. The combined dichloromethane phases are introduced into a precooled 20 l HC4 vessel and kept at 0° C.

1.37 kg (8.0 mol) of toluenesulphonamide in 6 l of toluene are introduced into a further 20 l HC4 vessel having a distillation bridge. The mixture is treated with 3.2 kg of 45% strength sodium hydroxide solution, 0.8 l of water and 130.5 g of tetrabutylammonium hydrogensulphate, heated to a maximum internal temperature of 40° C. and vacuum is applied. The previously obtained dichloromethane solution (15.2 l) is then added dropwise in the course of 1.5 hours and the dichloromethane is removed by distillation at 450 mbar at the same time (bath temperature: 60° C.). During the distillation, foam formation takes place. At the end, a solution with an internal temperature of 33–40° C. is present. After completion of the addition, further dichloromethane is removed by distillation until distillate barely still passes over (time: about 85 minutes; internal temperature 40° C. with a bath temperature of 60° C. at the end). The vessel contents are then transferred whilst still warm to a separating funnel and the vessel is rinsed at 50° C. with 5 l of water and 2 l of toluene. Before the phase separation, the solid constituents in the intermediate phase are filtered off with suction and washed with 0.5 l of toluene. The organic phase is washed with 2.4 l of water with stirring, separated off and evaporated to dryness in a rotary evaporator. The solid residue (1758 g) is suspended in 1.6 l of methanol at a bath temperature of 50° C., the suspension is transferred to a 10 l flask having a plane-ground joint and the flask is rinsed with 2.4 l of diisopropyl ether. The mixture is warmed to reflux temperature (59° C.) and stirred for a further 30 minutes under reflux. The suspension is cooled to 0° C., stirred at 0° C. for 1 hour, filtered off with suction and washed with 0.8 l of a cold mixture of methanol/diisopropyl ether (1:1.5). The crystallizate is dried at 50° C./400 mbar under a nitrogen atmosphere.

Example Z 10
3-(Toluene-4-sulphonyl)-6-oxa-3-aza-bicyclo[3.1.0]Hexane

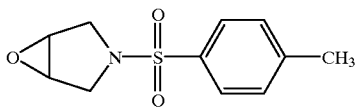

334.5 g (1.5 mol) of 1-(toluene-4-sulphonyl)-pyrroline are dissolved in 1.5 l of dichloromethane at room temperature and treated in the course of 15 minutes with a suspension of 408 g (about 1.65–1.77 mol) of 70–75% strength m-chloroperbenzoic acid in 900 ml of dichloromethane (cools during preparation). The mixture is heated under reflux for 16 hours (test for peroxide with KI/starch paper still indicates peroxide content), the suspension is cooled to 5° C., and the precipitated m-chlorobenzoic acid is filtered off with suction and washed with 300 ml of dichloromethane (peroxide test with precipitate: negative; precipitate discarded). The filtrate is washed twice with 300 ml of 10% strength sodium sulphite solution in each case to destroy excess peroxide (test for peroxide is now negative), extracted with 300 ml of saturated sodium bicarbonate solution, washed with water, dried using sodium sulphate and concentrated to about a quarter of the volume. Test for peroxide again: negative. The mixture is concentrated and the solid residue is stirred with 400 ml of isopropanol with ice-cooling, and the precipitate is filtered off with suction and dried in vacuo at 70° C.

Yield: 295 g (82.3%), m.p.: 136–139° C., TLC (dichloromethane/methanol98:2): 1 main component (iodine chamber).

Example Z 11
Trans-3-Hydroxy-4-(2-hydroxy-ethylamino)-1-(toluene-4-sulphonyl)-pyrrolidine

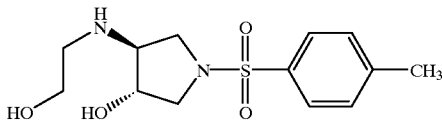

643.7 g (2.65 mol) of 3-(toluene-4-sulphonyl)-6-oxa-3-aza-bicyclo[3.1.0]hexane are refluxed for 16 hours with 318.5 ml of ethanolamine in 4 l of isopropanol. After TLC checking, a further 35.1 ml (altogether 5.86 mol) of ethanolamine are added to the mixture and it is boiled again until the next morning. The mixture is filtered off with suction whilst hot and the filtrate is concentrated to 3.5 ltr in a rotary evaporator. After seeding and stirring at room temperature, 3.5 l of diisopropyl ether are added and the mixture is stirred at 0° C. for 6 hours. The precipitated crystallizate is filtered off with suction, washed with 250 ml of a mixture of isopropanol/diisopropyl ether (1:1) and twice with 300 ml each of diisopropyl ether and dried overnight in a high vacuum.

Yield: 663.7 g (83% of theory), purity: 96.1% (area % according to HPLC.).

Example Z 12
{2-[[4-Hydroxy-1-(toluene-4-sulphonyl)-pyrrolidin-3-yl]-(toluene-4-sulphonyl)-amino]-ethyl} trans-toluene-4-sulphonate

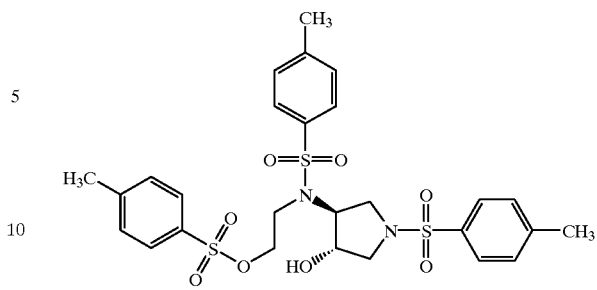

552 g (1.837 mol) of trans-3-hydroxy-4-(2-hydroxy-ethylamino)-1-(toluene-4-sulphonyl)-pyrrolidine are dissolved in 1.65 l of pyridine and 0.8 l of tetrahydrofuran under argon, and a total of 700 g (3.675 mol) of p-toluenesulphonylchloride is added at −10° C. in portions. The mixture is then stirred at this temperature for 16 hours. Working up is carried out by addition of 4.3 l of 18.5% strength aqueous hydrochloric acid, extraction twice with dichloromethane (3 l, 2 l), washing of the combined organic phases with saturated sodium hydrogencarbonate solution (3 l, 2 l), drying over sodium sulphate, filtering off with suction and removing the solvent by distillation in vacuo. The residue is dried overnight on an oil pump and employed in the next reaction in crude form. 1093 g resulted as a hard foam (purity [area % according to HPLC]: 80% tris-tosyl product and 13% tetra-tosyl product; yield see next stage).

Example Z 13
Rac. Trans-5.8-Bis-tosyl-2-oxa-5,6-diazabicyclo[4.3.0]Nonane

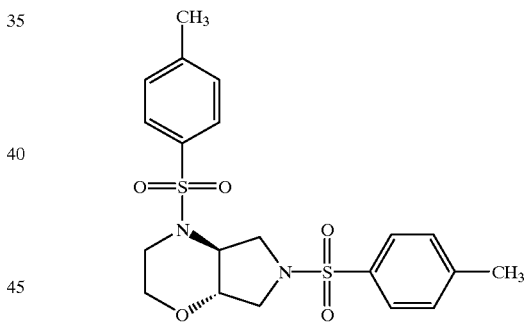

1092 g of crude {2-[[4-hydroxy-1-(toluene-4-sulphonyl)-pyrrolidin-3-yl]-(toluene-4-sulphonyl)-amino]-ethyl} trans-toluene-4-sulphonate are dissolved in 9.4 l of tetrahydrofuran and reacted at 0–3° C. with 1.4 l of a 1.43 molar solution of sodium hydroxide in methanol. After half an hour at this temperature, 2.1 l of water and 430 ml of dilute (2:1) acetic acid were added to the mixture and it is seeded with previously isolated crystals of {2-[[4-hydroxy-1-(toluene-4-sulphonyl)-pyrrolidin-3-yl]-(toluene-4-sulphonyl)-amino]-ethyl} trans-toluene-4-sulphonate. The suspension is stirred overnight at 0 to −4° C. Next morning, the crystals are filtered off with suction, washed twice with 400 ml each of a cold mixture of tetrahydrofuran/water (4:1) and dried at 50° C. overnight at 3 mbar.

Yield: 503 g of white crystals (62.7% of theory over 2 stages), Purity: 99.7% (area % according to HPLC.).

Example Z 14
Preparative Chromatographic Resolution of Rac. Trans-5,8-bis-tosyl-2-oxa-5,6-diazabicyclo[4.3.0]Nonane The chromatography of the racemate is carried out at room temperature in a column (internal diameter 75 mm), which is packed (bed height: about 38 cm) with 870 g of a chiral stationary phase (silica gel-bonded poly(N-methacryloyl-L-leucine-d-menthylamide) based on the mercapto-modified silica gel Polygosil 100, 10 µm; see EP-A-0 379 917). Detection is carried out with the aid of a UV detector at 254 nm. For the sample application, a solution of a concentration of 100 g of rac. trans-5,8-bis-tosyl-2-oxa-5,6-diazabicyclo[4.3.0]nonane in 3000 ml of tetrahydrofuran is used. A separation cycle is carried out under the following conditions: with the aid of a pump, at a flow of 50 ml/min, some of the sample solution and simultaneously, at a flow of 50 ml/min, pure n-heptane is transported to the column for 2 min. It is then eluted for 18 min using a mixture of n-heptane/tetrahydrofuran (3/2 vol/vol) at a flow of 100 ml/min. Elution with pure tetrahydrofuran then takes place for 3 min at a flow of 100 ml/min. Further elution with n-heptane/tetrahydro-furan(3/2 vol/vol) is then carried out. This cycle is repeated a number of times.

The initially eluted enantiomer is (1R,6R)-5,8-bis-tosyl-2-oxa-5,6-diazabicyclo-[4.3.0]nonane, which is isolated by concentration. The eluate of the more strongly retarding enantiomers is largely evaporated in vacuo, and the precipitated crystallizate is filtered off with suction and dried. In this manner, 86.1 g (96.2% of theory) of the enantiomer (1S,6S)-5,8-bis-tosyl-2-oxa-5,6-diazabicyclo[4.3.0]nonane having a purity of >99% ee are isolated from the separation of 179 g of racemate.

Example Z 15

(1R,6R)-2-Oxa-5,6-diazabicyclo[4.3.0]nonanedihydrobromide

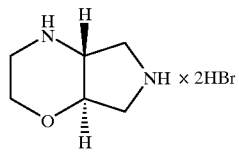

38.3 g (87 mmol) of (1R,6R)-5,8-bis-tosyl-2-oxa-5,6-diazabicyclo[4.3.0]nonane in 500 ml of 33% strength HBr/glacial acetic acid are treated with 10 g of anisole and heated at 60° C. (bath) for 4 hours. After standing overnight, the suspension is cooled, and the precipitate is filtered off with suction, washed with 100 ml of absol. ethanol and dried in a high vacuum at 70° C.

Yield: 23.5 g (93%) of white solid product, m.p.: 309–310° C. (dec.). TLC (dichloromethane/methanol/17% aq. ammonia 30:8:1): 1 main component, $[\alpha]_D$:+0.6° (c=0.53, H$_2$O) (varying).

Example Z 16

(1S,6S)-2-Oxa-5,6-diazabicyclo[4.3.0]nonanedihydrobromide

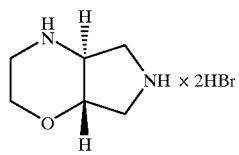

Analogously to Example Z 15, (1S,6S)-2-oxa-5,6-diazabicyclo[4.3.0]nonane dihydrobromide is obtained from (1S,6S)-5,8-bis-tosyl-2-oxa-5,6-diazabicyclo-[4.3.0]nonane.

Example Z 17

(1R,6R)-2-Oxa-5,8-diazabicyclo[4.3.0]nonane

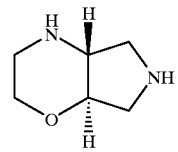

1st method: 5.8 g (20 mmol) of (1R,6R)-2-oxa-5,8-diazabicyclo[4.3.0]nonane dihydrobromide are suspended in 100 ml of isopropanol at room temperature, treated with 2.4 g (42.9 mmol) of powdered potassium hydroxide and left for about 1 hour in an ultrasonic bath. The suspension is cooled in an ice bath, filtered, the undissolved salt is washed with isopropanol and the filtrate is concentrated and distilled in a bulb tube oven at an oven temperature of 150–230° C. and 0.7 mbar. 2.25 g (87.9% of theory) of a viscous oil are obtained, which completely crystallizes. $[\alpha]_D$: −21.3° (c=0.92, CHCl$_3$) Correspondingly, this reaction can also be carried out in ethanol.

2nd method: A homogenized mixture of (1R,6R)-2-oxa-5,8-diazabicyclo[4.3.0]nonane dihydrobromide and 620 mg (11 mmol) of powdered potassium hydroxide is distilled dry in a bulb tube apparatus at 0.2 mbar and increasing oven temperature to 250° C. 490 mg (76.6% of theory) of (1R,6R)-2-oxa-5,8-diazabicyclo[4.3.0]nonane are obtained as a viscous oil, which slowly crystallizes.

3rd method: 100 g of moist, pretreated cation exchanger (Dowex 50WX, H$^+$ form, 100–200 mesh, capacity: 5.1 meq/g dry or 1.7 meq/ml) are packed into a column, activated with about 200 ml of 1 N HCl and washed with 3 l of water until neutral. A solution of 2.9 g (10 mmol) of (1R,6R)-2-oxa-5,8-diazabicyclo[4.3.0]nonane dihydrobromide in 15 ml of water is added to the ion exchanger and then washed with 2 l of water and eluted with 1 l of about 1N ammonia solution. The eluate is concentrated in vacuo.

Yield: 1.3 g of viscous oil (quant.), TLC (dichloromethane/methanol/17% NH$_3$ 30:8:1): 1 main component, GC: 99.6% (area).

Example Z 18

(1S,6S)-2-Oxa-5,8-diazabicyclo[4.3.0]nonane

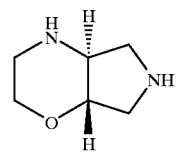

Analogously to Example Z 17, the free base (1S,6S)-2-oxa-5,8-diazabicyclo[4.3.0]nonane is prepared from (1S,6S)-2-oxa-5,8-diazabicyclo[4.3.0]nonane dihydrobromide.

Example Z 19
Ethyl 2-(2,4-dichloro-3-cyano-5-fluoro-benzoyl)-3-dimethylamino-acrylate

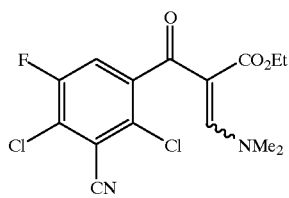

1

Starting at room temperature, a solution of 1075 g of 2,4-dichloro-3-cyano-5-fluorobenzoyl chloride (about 94% strength, corresponding to 1010.5 g=4.00 mol) in 850 ml of dichloromethane is added dropwise to a solution of 626 g (4.372 mol) of ethyl 3-dimethylamino-acrylate and 591 g (4.572 mol) of ethyl diisopropyl-amine (Hünig's base) in 1060 ml of dichloromethane. In the course of this, the temperature rises to about 50–55° C. (dropwise addition time about 90 minutes). The reaction mixture is subsequently stirred at 50° C. for 2 hours and then employed in the next stage without further working up.

Example Z 20
Ethyl 2-(2,4-dichloro-3-cyano-5-fluoro-benzoyl)-3-cyclopropylamino-acrylate

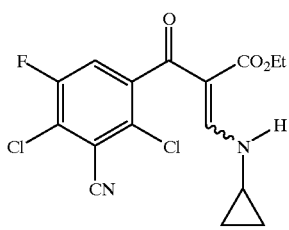

2

306 g (5.1 mol) of glacial acetic acid are added dropwise at about 15° C. with cooling to the reaction mixture from the above stage. 267.3 g (4.68 mol) of cyclopropylamine are then added dropwise at about 10–15° C. with further cooling. Immediately after this, the reaction mixture is treated with 1300 ml of water with ice-cooling and stirred well for 15 minutes. The dichloromethane phase is separated off and employed in the next stage.

Example Z 21
Ethyl 7-chloro-8-cyano-1-cyclopropyl-6-fluoro-1,4-dihydro-4-oxo-3-quinoline-carboxylate

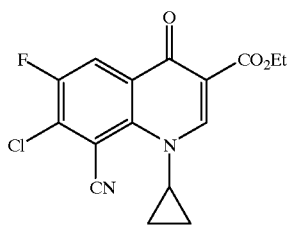

3

The dichloromethane phase from the previous stage is added dropwise (about 90 minutes) to a suspension of 353 g (2.554 mol) of potassium carbonate in 850 ml of N-methylpyrrolidone heated to 60–70° C. During the addition, dichloromethane is simultaneously removed from the reaction mixture by distillation. The reaction mixture is then stirred well at 60–70° C. for a further 5½ hours. It is allowed to cool to about 50° C. and residual dichloromethane is removed by distillation under a vacuum of about 250 mbar. 107 ml of 30% strength hydrochloric acid are then added dropwise at room temperature with ice-cooling, whereby a pH of 5–6 is established. 2200 ml of water are then added with ice-cooling. The reaction mixture is well stirred for 15 minutes, and the solid is then filtered off with suction and washed twice with 1000 ml each of water and three times with 1000 ml each of ethanol on the suction filter and then dried at 60° C. in a vacuum drying oven.

Yield: 1200 g (89.6% of theory).

This product can optionally be further purified by stirring the solid under reflux for 30 minutes in 2000 ml of ethanol. It is filtered off with suction whilst hot, washed with 500 ml of ethanol and dried at 60° C. in vacuo.

Melting point: 180–182° C.

$^1$H-NMR (400 MHz, CDCl$_3$): d=1.2–1.27 (m; 2H), 1.41 (t; 3H); 1.5–1.56 (m; 2H), 4.1–4.8 (m; 1H), 4.40 (q; 2H), 8.44 (d, J=8.2 Hz; H), 8.64 (s; 1H) ppm.

Example Z 22
7-Chloro-8-cyano-1-cyclopropyl-6-fluoro-1,4-dihydro-4-oxo-3-quinolinecarboxylic Acid

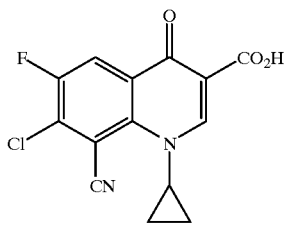

4

33.8 g (0.1 mol) of ethyl 7-chloro-8-cyano-1-cyclopropyl-6-fluoro-1,4-dihydro-4-oxo-3-quinolinecarboxylate are heated under reflux for 3 hours in a mixture of 100 ml of acetic acid, 20 ml of water and 10 ml of concentrated sulphuric acid. After cooling, the mixture is poured onto 100 ml of ice water, and the deposited precipitate is filtered off with suction, washed with water and ethanol and dried in vacuo at 60° C.

Yield: 29.6 g (96% of theory), melting point: 276–277° C. (with decomposition).

Preparation of the Active Compounds

Example 1

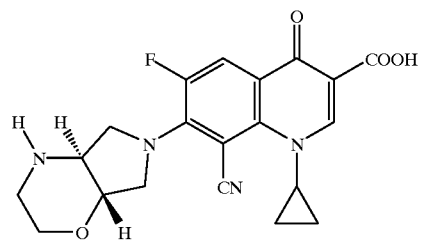

A) 8-Cyano-1-cyclopropyl-6-fluoro-7-((1S,6S)-2-oxa-5,8-diazabicyclo[4.3.0]on-8-yl)-1,4-dihydro-4-oxo-3-quinolinecarboxylic Acid 1.00 g (3.26 mmol) of 7-chloro-8-cyano-1-cyclopropyl-6-fluoro-1,4-dihydro-4-oxo-3-quinolinecarboxylic acid are stirred under argon at 40–45° C. for 25 hours with 501 mg (3.91 mmol) of (1S,6S)-2-oxa-5,8-diazabicyclo[4.3.0]nonane and 0.9 ml of triethylamine in 30 ml of acetonitrile. All volatile components are removed in vacuo and the residue is recrystallized from ethanol.

Yield: 1.22 g (94%); Melting point: 294° C. (with decomposition).

B) 8-Cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic Acid Hydrochloride 200 mg (0.63 mmol) of ethyl 8-cyano-1-cyclopropyl-6,7-difluoro-1,4-dihydro-4-oxo-3-quinolinecarboxylate are stirred under argon at 40–45° C. for 2 hours with 97 mg (0.75 mmol) of (1S,6S)-2-oxa-5,8-diazabicyclo[4.3.0]nonane and 0.17 ml of triethylamine in 3 ml of acetonitrile. All volatile components are removed in vacuo, the residue is treated with water, insoluble material is filtered off and the filtrate is extracted with dichloromethane. The organic phase is dried over sodium sulphate and then concentrated in vacuo. The resulting residue is dissolved in 6 ml of tetrahydrofuran and 2 ml of water and treated with 30 mg (0.72 mmol) of lithium hydroxide monohydrate. After stirring at room temperature for 16 hours, (he mixture is acidified with dil. hydrochloric acid and the resulting precipitate is filtered off with suction and dried.

Yield: 155 mg (57%); Melting point: >300° C.

C) 8-Cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic Acid Hydrochloride 1 g (2.5 mmol) of 8-cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic acid is suspended in 20 ml of water, and the suspension is treated with 10 ml of 1N hydrochloric acid and stirred at room temperature for 3 hours. The precipitate obtained is filtered off with suction, washed with ethanol and dried at 80° C. in a high vacuum.

Yield: 987 mg (90.6% of theory), Melting point: 314–316° C. (with decomposition).

D) 8-Cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic Acid Hydrochloride 86.4 g (217 mmol) of 8-cyano-1-cyclopropyl-6-fluoro-7-((1S,6S)-2-oxa-5,8-diazabicyclo[4.3.0]non-8-yl)-1,4-dihydro-4-oxo-3-quinolinecarboxylic acid are dissolved in 963 ml of water and 239 ml of 1N aqueous sodium hydroxide solution at room temperature. After filtration and washing with 20 ml of water, the mixture is treated with 477 ml of 1N aqueous hydrochloric acid and the precipitated crystallizate is dissolved at 95° C. to 100° C. The solution is cooled overnight, and the precipitated crystallizate is filtered off with suction and washed three times with 500 ml of water each time and dried in vacuo.

Yield: 90 g (94.7% of theory), purity: >99% (area % according to HPLC.); 99.6% ee.

$[\alpha]_D^{23}$: −112° (c=0.29, 1N NaOH).

Example 2

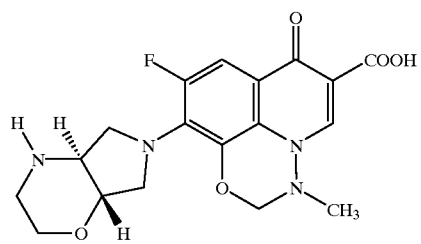

9-Fluoro-3-methyl-10-((1S,6S)-2-oxa-5,8-diazabicyclo[4.3.0]non-8-yl)-7-oxo-2,3-dihydro-7H-pyrido[1,2,3-d,e][1,3,4]benzoxadiazine-6-carboxylic Acid 100 mg (0.354 mmol) of 9,10-difluoro-3-methyl-7-oxo-2,3-dihydro-7H-pyrido[1,2,3-d,e]-[1,3,4]benzoxadiazine-6-carboxylic acid are heated under argon at 120° C. for one hour with 91 mg (0.71 mmol) of (1S,6S)-2-oxa-5,8-diazabicyclo[4.3.0]nonane in 3 ml of DMSO. The mixture is concentrated in a high vacuum, and the residue is recrystallized from ethanol and dried.

Yield: 106 mg (77% of theory); Melting point: 205° C. (with decomposition).

Example 3

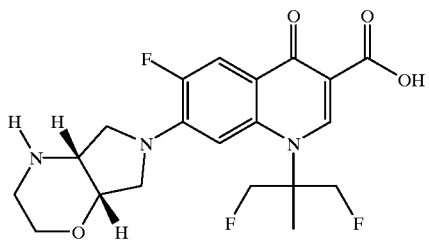

1-(1-Fluoromethyl-1-methyl-2-fluoroethyl)-6-fluoro-7-[(1S,6R)-2-oxa-5,8-diazabicyclo[4.3.0]non-8-yl]-1,4-dihydro-4-oxo-3-quinolinecarboxylic Acid A solution of 1-(1-fluoromethyl-1-methyl-2-fluoroethyl)-6,7-difluoro-1,4-dihydro-4-oxo-3-quinolinecarboxylic acid (400 mg, 1.26 mmol), (1S,6R)-2-oxa-5,8-diazabicyclo[4.3.0]nonane (176 mg, 1.39 mmol) and 1,4-diazabicyclo[2.2.2]octane (141 mg, 1.26 mmol) in absol. acetonitrile (20 ml) is heated under reflux overnight. After cooling the reaction mixture to room temperature, the precipitated crystals are filtered off and washed with acetonitrile.

Yield: 392 mg (73% of theory); Melting point: 245° C.

Example 4

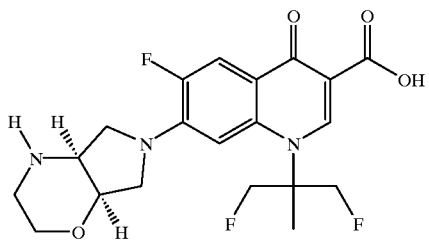

1-(1-Fluoromethyl-1-methyl-2-fluoroethyl)-6-fluoro-7-[(1R,6S)-2-oxa-5,8-diazabicyclo[4.3.0]non-8-yl]-1,4-dihydro-4-oxo-3-quinolinecarboxylic Acid The title compound is prepared analogously to the procedure of Example 3 by reaction with (1R,6S)-2-oxa-5,8-diazabicyclo[4.3.0]nonane.

Yield: 58% of theory; Melting point: >250° C.

Example 5

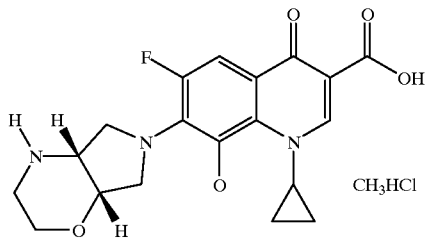

1-(Cyclopropyl)-6-fluoro-8-methoxy-7-[(1S,6R)-2-oxa-5,8-diazabicyclo[4.3.0]non-8-yl]-1,4-dihydro-4-oxo-3-quinolinecarboxylic Acid Hydrochloride The title compound is prepared analogously to the procedure of Example 3 by reaction with (1S,6R)-2-oxa-5,8-diazabicyclo[4.3.0]nonane. The crude product is purified by column chromatography (CH$_2$Cl$_2$/MeOH/AcOH, 10:5:0.5), the product being obtained as an acetate salt. After addition of methanol and 1N HCl and concentration of the solution in vacuo, the hydrochloride is obtained in crystalline form.

Yield: 67% of theory; Melting point: >250° C.

Example 6

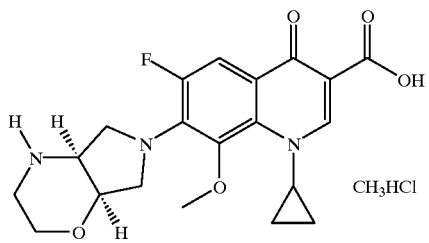

1-Cyclopropyl-6-fluoro-8-methoxy-7-[(1R,6S)-2-oxa-5,8-diazabicyclo[4.3.0]non-8-yl]-1,4-dihydro-4-oxo-3-quinolinecarboxylic Acid Hydrochloride The title compound is prepared analogously to the procedure of Example 5 by reaction with (1R,6S)-2-oxa-5,8-diazabicyclo[4.3.0]nonane.

Yield: 37% of theory; Melting point: >250° C.

Example 7

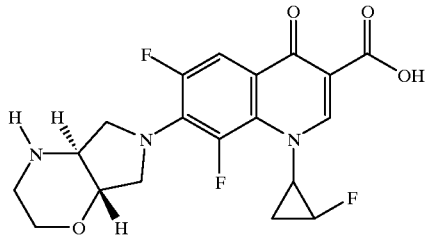

1-(cis-2-Fluorocyclopropyl)-6,8-difluoro-1,4-dihydro-7-(1S,6S-2-oxa-5,8-diazabicyclo[4.3.0]non-8-yl)-4-oxo-3-quinolinecarboxylic Acid A mixture of 3.6 g (12 mmol) of 1-(cis-2-fluorocyclopropyl)-6,7,8-trifluoro-1,4-dihydro-4-oxo-3-quinolinecarboxylic acid in 50 ml ml of acetonitrile and 25 ml of dimethylformamide is heated under reflux for 1 hour with 3.36 g (30 mmol) of 1,4-diazabicyclo[2.2.2]octane and 3.7 g (12.8 mmol) of 1S,6S-2-oxa-5,8-diazabicyclo[4.3.0]nonane dihydrobromide. The mixture is concentrated, and the residue is mixed with some water and treated in an ultrasonic bath for 30 minutes. The undissolved precipitate is filtered off with suction, washed with water and dried at 80° C. in a high vacuum.

Yield: 4.2 g (86% of theory); Melting point: 274–276° C. (with decomposition).

Example 8

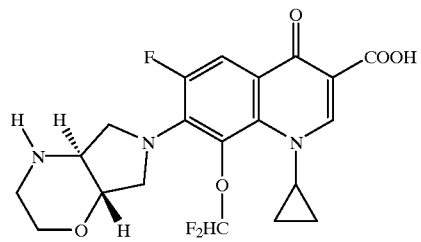

1-Cyclopropyl-8-difluoromethoxy-6-fluoro-1,4-dihydro-7-((1S,6S)-2-oxa-5,8-diazabicyclo[4.3.0]non-8-yl)-4-oxo-3-quinolinecarboxylic Acid A mixture of 166 mg (0.5 mmol) of 1-cyclopropyl-8-difluoromethoxy-6,7-difluoro-1,4-dihydro-4-oxo-3-quinolinecarboxylic acid in 1.5 ml ml of acetonitrile and 0.75 ml of dimethylformamide is heated under reflux for 1 hour with 73 mg (0.65 mmol) of 1,4-diazabicyclo[2.2.2] octane and 100 mg (0.78 mmol) of 1S,6S-2-oxa-5,8-diazabicyclo[4.3.0]nonane. The mixture is concentrated, and the residue is mixed with some water and treated in an ultrasonic bath for 20 minutes. The undissolved precipitate is filtered off with suction, washed with water and dried at 80° C. in a high vacuum.

Yield: 164 mg (75% of theory); Melting point: 209–21 ° C. (with decomposition).

$[\alpha]_D^{25}$: −250° (c=0.25, DMF).

Example 9

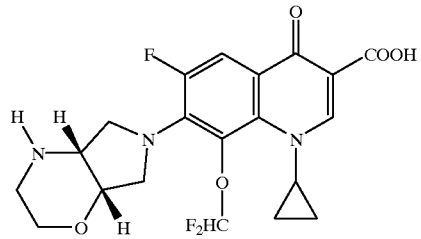

Analogously to Example 8, 1-cyclopropyl-8-difluoromethoxy-6-fluoro-1,4-dihydro-7-((1S,6R)-2-oxa-5,8-diazabicyclo[4.3.0]non-8-yl)-4-oxo-3-quinolinecarboxylic acid is obtained of melting point: 181–182° C. (with decomposition).

$[\alpha]_D^{25}$EQ: −23° (c=0.25, DMF).

Example 10

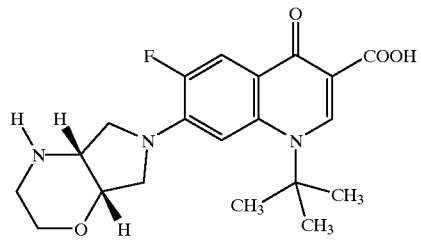

Analogously to Example 8, 1-tert-butyl-6-fluoro-1,4-dihydro-7-((1S,6R)-2-oxa-5,8-diazabicyclo[4.3.0]non-8-yl)-4-oxo-3-quinolinecarboxylic acid is obtained of melting point: 224–226° C. (with decomposition).

$[\alpha]_D^{25}$: +70° (C=0.25, DMF).

Example 11

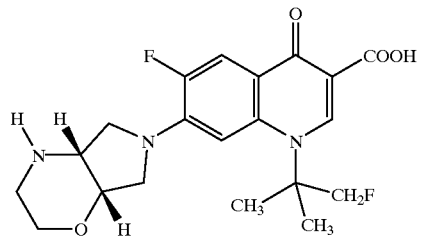

Analogously to Example 8, 6-fluoro-1-(fluoro-tert-butyl)-1,4-dihydro-7-((1S,6R)-2-oxa-5,8-diazabicyclo[4.3.0]non-8-yl)-4-oxo-3-quinolinecarboxylic acid is obtained of melting point: 243–244° C. (with decomposition).

$[\alpha]_D^{25}$: +71° (c=0.25, DMF).

Example 12

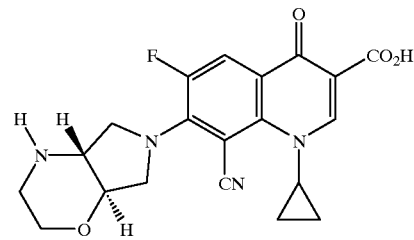

A) 8-Cyano-1-cyclopropyl-6-fluoro-7-((1R,6R)-2-oxa-5,8-diazabicyclo[4.3.0]non-8-yl)-1,4-dihydro-4-oxo-3-quinolinecarboxylic Acid 1st method: 310 mg (1 mmol) of 7-chloro-8-cyano-1-cyclopropyl-6-fluoro-1,4-dihydro-4-oxo-3-quinolinecarboxylic acid are heated under reflux for 1 hour with 300 mg (1.05 mmol) of (1R,6R)-2-oxa-5,8-diazabicyclo[4.3.0]nonane dihydrobromide and 610 mg (6 mmol) of triethylamine in a mixture of 4 ml of acetonitrile and 2 ml of DMF. According to TLC and HPLC, 7-chloro-8-cyano-1-cyclopropyl-6-fluoro-1,4-dihydro-4-oxo-3-quinolinecarboxylic acid is no longer detectable. The mixture is placed in the refrigerator overnight for crystallization, and the precipitate is filtered off with suction, washed with water and dried at 80° C. in a high vacuum.

Yield: 335 mg (84%), melting point: 295–296° C. (with decomposition).

2nd method: 920 mg (3 mmol) of 7-chloro-8-cyano-1-cyclopropyl-6-fluoro-1,4-dihydro-4-oxo-3-quinolinecarboxylic acid are stirred under nitrogen for 4 hours at 45° C. with 480 mg (3.75 mmol) of (1R,6R)-2-oxa-5,8-diazabicyclo[4.3.0]nonane and 0.9 ml of triethylamine in 25 ml of acetonitrile; addition of a further 0.5 ml of triethylamine, then stirred at 60° C. for a further 16 hours. The suspension is cooled in an ice bath, and the precipitate is filtered off with suction, washed with ethanol and dried at 70° C. in vacuo.

Yield: 1.05 g (88%), melting point: 294° C. (with decomposition), $[\alpha]_D$: +103.6° (c=0.33; 1N NaOH), HPLC: 99.9% (area).

B) 8-Cyano-1-cyclopropyl-6-fluoro-7-((1 R,6R)-2-oxa-5,8-diazabicyclo[4.3.0]non-8-yl)-1,4-dihydro-4-oxo-3-quinolinecarboxylic Acid Hydrochloride Analogously to Example 1C, 8-cyano-1-cyclopropyl-6-fluoro-7-((1R,6R)-2-oxa-5,8-diazabicyclo[4.3.0]non-8-yl)-1,4-dihydro-4-oxo-3-quinolinecarboxylic acid is reacted with hydrochloric acid.

Example 13

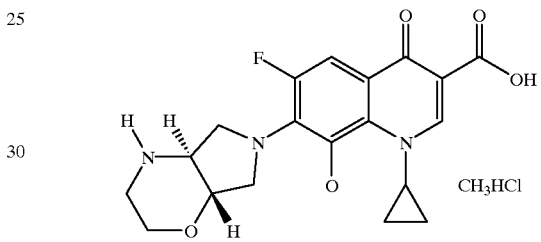

1-Cyclopropyl-6-fluoro-8-methoxy-7-((1S,6S)-2-oxa-5,8-diazabicyclo[4.3.0]nonan-8-yl-1,4-dihydro-4-oxo-3-quinolinecarboxylic Acid Hydrochloride The title compound is prepared analogously to the procedure of Example 5 by reaction with (1S,6S)-2-oxa-5,8-diazabicyclo[4.3.0]nonane. The crude product is purified by column chromatography ($CH_2Cl_2$/MeOH/AcOH, 10:5:0.5), the product being obtained as an acetate salt. After addition of methanol and 1N HCl and concentration of the solution in vacuo, the hydrochloride is obtained in crystalline form.

Melting point: >250° C.

Example 14

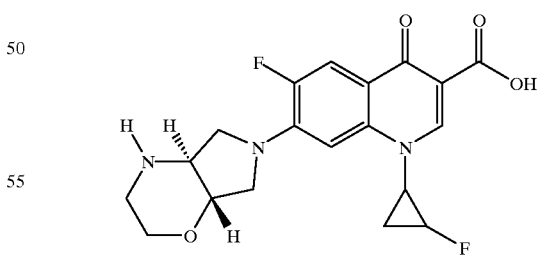

6-Fluoro-1-((1R,2S)-2-fluorocyclopropyl)-7-((1S,6S)-2-oxa-5,8-diazabicyclo[4.3.0]nonan-8-yl)-1,4-dihydro-4-oxo-3-quinolinecarboxylic Acid The title compound is prepared analogously to the procedure of Example 8 by reaction of 6,7-difluoro-1-((1R,2S)-2-fluorocyclopropyl)-1,4-dihydro-4-oxo-3-quinolinecarboxylic acid with (1S,6S)-2-oxa-5,8-diazabicyclo[4.3.0]nonane.

Melting point: >250° C.

Examples 15–21

Analogously to Example 8, using (1R,6S)-2-oxa-5,8-diazabicyclo[4.3.0]nonane the following compounds are obtained, which in some cases were isolated as hydrochlorides by dissolving in half-concentrated hydrochloric acid, evaporating and treating with ethanol:

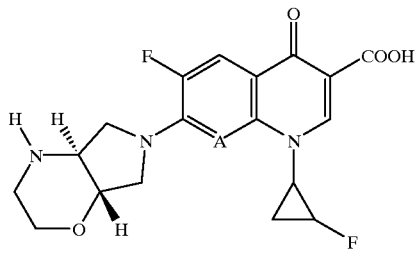

Example 15

6-Fluoro-1-(cis-2-fluorocyclopropyl)-1,4-dihydro-7-((1R,6S)-2-oxa-5,8-diazabicyclo[4.3.0]non-8-yl)-4-oxo-3-quinolinecarboxylic acid (A=CH), melting point: 236–238° C. (with decomposition);

Example 16

6,8-Difluoro-1-(cis-2-fluorocyclopropyl)-1,4-dihydro-7-((1R,6S)-2-oxa-5,8-diazabicyclo[4.3.0]non-8-yl)-4-oxo-3-quinolinecarboxylic acid hydrochloride (A=CF;xHCl), melting point: 275–280° C. (with decomposition);

Example 17

8-Chloro-6-fluoro-1-(cis-2-fluorocyclopropyl)-1,4-dihydro-7-((1R,6S)-2-oxa-5,8-diazabicyclo[4.3.0]non-8-yl)-4-oxo-3-quinolinecarboxylic acid hydrochloride (A=CCl;xHCl), melting point: 210–215° C. (with decomposition);

Example 18

6-Fluoro-1-(cis-2-fluorocyclopropyl)-1,4-dihydro-7-((1R,6S)-2-oxa-5,8-diazabicyclo[4.3.0]non-8-yl)-4-oxo-1,8-naphthyridine-3-carboxylic acid hydrochloride (A=N;x HCl), melting point: 281–284° C. (with decomposition);

Example 19

6-Fluoro-1-(trans-2-fluorocyclopropyl)-1,4-dihydro-7-((1R,6S)-2-oxa-5,8-diazabicyclo[4.3.0]non-8-yl)-4-oxo-3-quinolinecarboxylic acid (A=CH), melting point: 270–274° C. (with decomposition);

Example 20

8-Chloro-6-fluoro-1-(trans-2-fluorocyclopropyl)-1,4-dihydro-7-((1R,6S)-2-oxa-5,8-diazabicyclo[4.3.0]non-8-yl)-4-oxo-3-quinolinecarboxylic acid (A=CCl), melting point: 160–164° C. (with decomposition);

Example 21

6-fluoro-1-(trans-2-fluorocyclopropyl)-1,4-dihydro-7-((1R,6S)-2-oxa-5,8-diazabicyclo[4.3.0]non-8-yl)-4-oxo-1,8-naphthyridine-3-carboxylic acid (A=N), melting point: 310–314° C. (with decomposition).

What is claimed is:

1. A compound which is 8-cyano-1-cyclopropyl-6-fluoro-7-((1S,6S)-2-oxa-5,8-diazabicyclo [4.3.0]-non-8-yl)-1,4-dihydro-4-oxo-3-quinoline carboxylic acid of the formula:

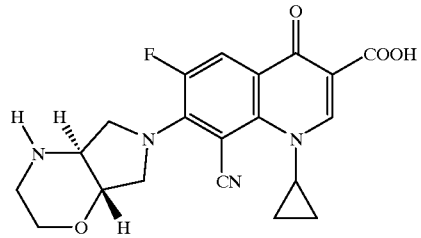

or a pharmaceutically utilizable hydrate and/or salt thereof.

2. A pharmaceutical composition comprising the compound according to claim 1 and a pharmaceutically utilizable carrier.

3. A method for treating a Helicobacter pylori infection and/or a gastroduodenal disorder associated with a Helicobacter pylori infection, said method comprising administering to a patient an effective amount therefor of the compound according to claim 1.

* * * * *

UNITED STATES PATENT AND TRADEMARK OFFICE
CERTIFICATE OF CORRECTION

PATENT NO.    : 6,133,260
DATED         : October 17, 2000
INVENTOR(S)   : Michael Matzke et al.

Page 1 of 1

It is certified that error appears in the above-identified patent and that said Letters Patent is hereby corrected as shown below:

<u>Column 25,</u>
Example 5, please delete the formula and insert the following:

--

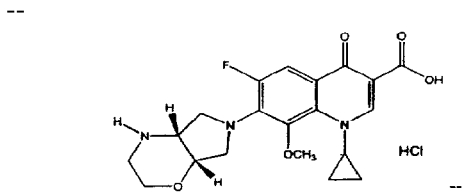

--

Example 6, please delete the formula and insert the following:

--

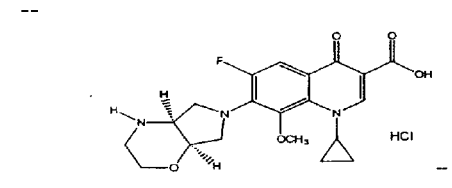

--

<u>Column 28,</u>
Example 13, please delete the formula and insert the following:

--

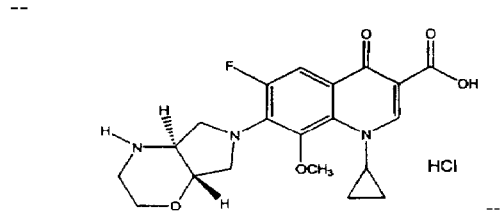

--

Signed and Sealed this

Twentieth Day of August, 2002

Attest:

*Attesting Officer*

JAMES E. ROGAN
*Director of the United States Patent and Trademark Office*